(12) United States Patent
Khorana

(10) Patent No.: US 10,722,415 B2
(45) Date of Patent: Jul. 28, 2020

(54) JOINT POWER

(71) Applicant: Rahul Khorana, San Jose, CA (US)

(72) Inventor: Rahul Khorana, San Jose, CA (US)

( * ) Notice: Subject to any disclaimer, the term of this patent is extended or adjusted under 35 U.S.C. 154(b) by 460 days.

(21) Appl. No.: 15/706,272

(22) Filed: Sep. 15, 2017

(65) Prior Publication Data
US 2019/0083347 A1 Mar. 21, 2019

(51) Int. Cl.
| | |
|---|---|
| *B25J 9/00* | (2006.01) |
| *A61F 5/00* | (2006.01) |
| *A61H 1/02* | (2006.01) |
| *A63B 21/00* | (2006.01) |
| *A63B 21/005* | (2006.01) |
| *A61F 2/72* | (2006.01) |
| *A61H 3/00* | (2006.01) |
| *A61F 2/50* | (2006.01) |
| *A61F 2/70* | (2006.01) |

(52) U.S. Cl.
CPC .............. *A61H 1/024* (2013.01); *A61F 2/72* (2013.01); *A61H 1/02* (2013.01); *A61H 1/0277* (2013.01); *A61H 3/00* (2013.01); *A63B 21/0059* (2015.10); *A63B 21/00178* (2013.01); *A63B 21/00181* (2013.01); *A61F 2002/5038* (2013.01); *A61F 2002/704* (2013.01); *A61F 2002/707* (2013.01); *A61H 2201/0161* (2013.01); *A61H 2201/1215* (2013.01); *A61H 2201/1223* (2013.01); *A61H 2201/165* (2013.01); *A61H 2201/1676* (2013.01); *A61H 2201/501* (2013.01); *A61H 2201/5012* (2013.01); *A61H 2201/5043* (2013.01); *A61H 2201/5061* (2013.01); *A61H 2201/5069* (2013.01); *A61H 2201/5097* (2013.01); *A61H 2203/0406* (2013.01); *A61H 2203/0431* (2013.01); *A61H 2230/08* (2013.01); *A61H 2230/50* (2013.01); *A63B 2209/00* (2013.01); *A63B 2209/10* (2013.01); *A63B 2210/50* (2013.01); *A63B 2220/51* (2013.01); *A63B 2220/836* (2013.01); *A63B 2225/20* (2013.01); *A63B 2225/50* (2013.01); *A63B 2230/105* (2013.01); *A63B 2230/50* (2013.01); *A63B 2230/605* (2013.01)

(58) Field of Classification Search
CPC ....... A61F 2/25; A63B 21/0081; B25J 9/0006
USPC ..................................................... 601/34, 35
See application file for complete search history.

(56) References Cited

U.S. PATENT DOCUMENTS

| | | | |
|---|---|---|---|
| 6,872,187 B1 * | 3/2005 | Stark ................. | A61F 5/0102 602/16 |
| 8,690,802 B2 | 4/2014 | Sankai | |
| 9,216,131 B2 | 12/2015 | Nakashima | |
| 2008/0071386 A1 * | 3/2008 | McBean ............. | A61F 5/0127 623/25 |
| 2015/0150708 A1 * | 6/2015 | Paez ................... | A61F 5/0123 602/16 |

* cited by examiner

*Primary Examiner* — Bruce E Snow
(74) *Attorney, Agent, or Firm* — Patent Law Office, PC; Bao Tran

(57) ABSTRACT

Systems and methods are disclosed for assisting body motion by attaching a plurality of rods to a body; sensing movement parameters with sensors coupled to the rods; transmitting the movement parameters to a wearable device and receiving actuation commands from the wearable device; and based on the received commands, actuating the rods with one or more actuators.

15 Claims, 2 Drawing Sheets

JOINT POWER

The present system relates to a motion-assist system using a motion-assist device.

BACKGROUND

In recent years, motion-assist devices have been developed, separately from autonomous robots. A motion-assist device is wearable by a human body for assisting human activity of the human body. The motion-assist device assists the motion of the wearer. The assistance is implemented by acquiring bioelectrical signals (biological information including, for example, myoelectric potential signals, neurotransmission signals, and brain wave detection signals) of the wearer, and supplying power in accordance with the intention of the wearer, to an actuator of the motion-assist device, based on the acquired bioelectrical signals. Meanwhile, it is known that doctors and physical therapists conduct rehabilitation for patients who cannot move their bodies due to factors such as age, cerebral apoplexy and spinal cord injury, for the purpose of recovering muscle strength and preventing muscle strength from declining.

SUMMARY

Systems and methods are disclosed for assisting body motion by attaching a plurality of rods to a body; sensing movement parameters with sensors coupled to the rods; transmitting the movement parameters to a wearable device and receiving actuation commands from the wearable device; and based on the received commands, actuating the rods with one or more actuators.

Implementations of the above aspect may include one or more of the following. The wearable device can be a smart watch or a mobile device for receiving an instruction from a person to move a rod to a selected position, the combination of movements allowing the person to ambulate, compensate for body weakness, or rehabilitate the body. The wearable device can control power, rate of opening or closing and direction of the rods using the wearable device. The motors can receive actuating commands over a wireless network or a wired network. The motors can receive actuating commands from a rehabilitation specialist operating remotely from the wearable device. A cloth mesh can be secured to a pair of rods for providing a grip between the device and the patient. Five rods can be placed in an H-configuration and actuated by two motors, one on each leg. The rods can be secured around a person's torso and legs and assisting the person to move from a bed, a toilet, or a seat. The rods can be attached to a person's knee or elbow to help mobility of the knee or elbow. The rods can be folded to minimize storage space when not on a person.

Advantages may include one or more of the following. The system helps those with limited mobility or no mobility to be able to supplement their muscles with motorized rods that can move a person's body to a desired position. The system provides a motion-assist system in the form of a motion-assist device, a motion-assist device, and a motion-assist method of the motion-assist device, with which the state of a target of motion assistance, such as a patient or a trainee, can be objectively recognized to effectively conduct motion assistance such as rehabilitation and training. The system provides a wireless communication where a doctor can recognize the state of a patient via a network and appropriately conduct rehabilitation for the patient wearing the motion-assist device, even when the doctor and the patient are at remote locations from one another.

DESCRIPTION

A description is given, with reference to the accompanying drawings, of a motion-assist system using a motion-assist device according to an embodiment of the present system. In the present embodiment, a doctor and a patient are described as targets of the motion-assist system, to which the present system is not limited. For example, a trainer and a trainee may be the targets. As a matter of course, the present system is applicable to anyone who is in need of motion assistance.

Figure 1:
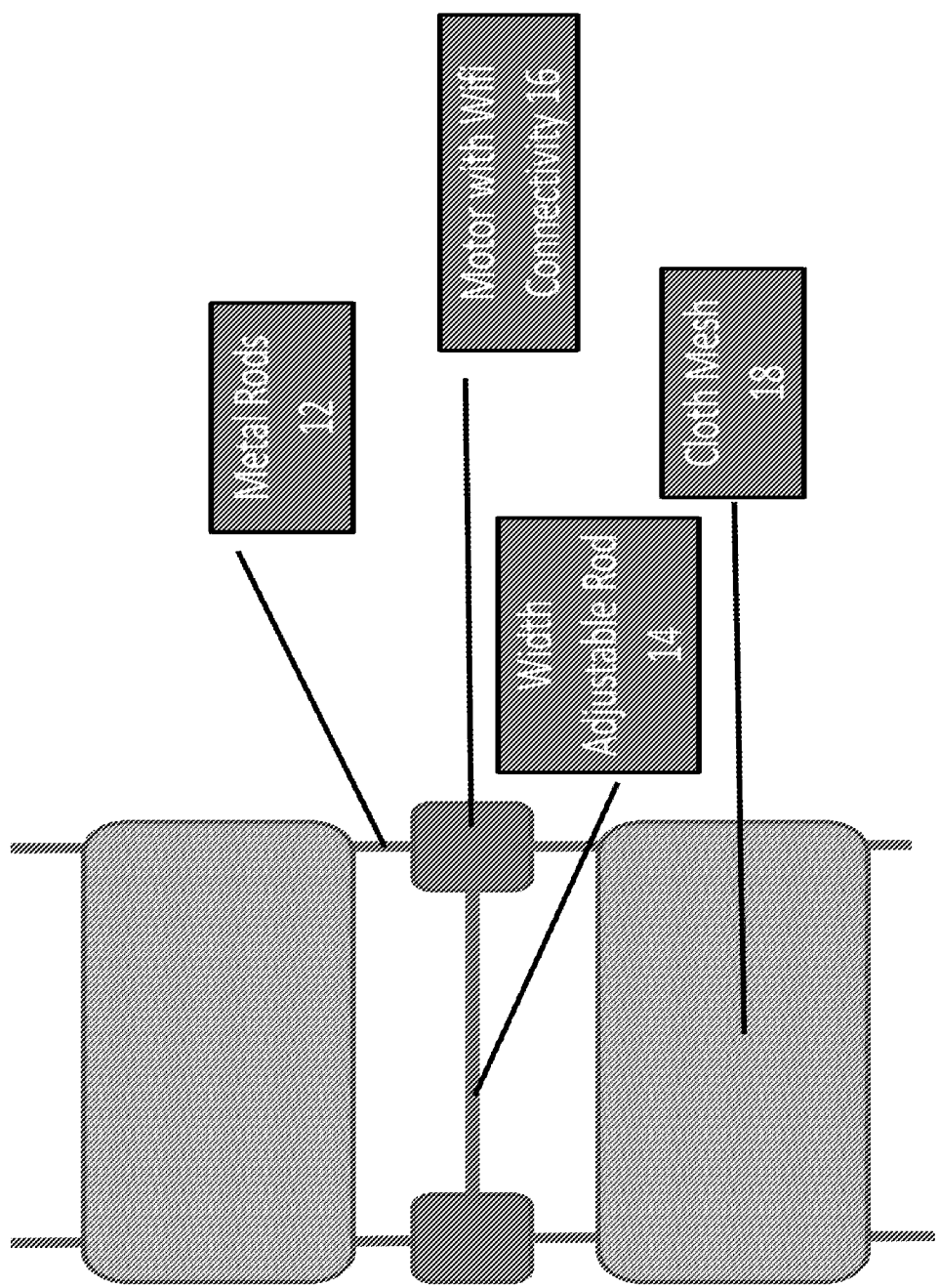
FIG. 1 schematically illustrates a usage environment of a motion-assist system of a motion-assist device according to an embodiment of the present system.
Figure 1:

FIG. 1 schematically illustrates a usage environment of a motion-assist system of a motion-assist device according to one embodiment. A user wearable device 10 such as a watch controls a plurality of moveable rods 12. The rods 12 are actuated by motor(s) 16 through a controller with wireless connectivity such as WiFi or Bluetooth communication. A cloth mesh 18 connects each pair of two rods 12.

The motor 16, through the controller with the wireless connectivity, can be managed by the motion assist device 10 or by a remote user such as a doctor. For local control via the wearable device 10, the network may be a wireless network, for example, Bluetooth or a public wireless LAN such as IEEE802.11a/b/g/n, among others. For remote control, when the doctor and the patient are at different locations, the network 3 may be a wired network such as a public telephone line or the Internet. Thus, communications can be performed between them via a wired network or the Internet.

In one embodiment, the device has 5 rods, in H-configuration and has 2 motors, one on each leg. This device can be secured to a patient who has trouble moving the joint. The mesh clothing 18 provides a grip between the device and the patient. Once in place, the patient can use the smart watch 10 to control the device. The user can control the power, rate of opening or closing and the direction of the device.

A number of sensors can be used to measure positioning and body data. For example, a force sensor is used for measuring the force applied to the rods. For example, the force sensor includes a strain gauge for detecting the strain caused by the applied force, and outputs electric signals proportional to strain. The force sensor is disposed at a hinge that bends due to the driving torque from the actuator unit. A bioelectrical signal detecting unit can be used for detecting bioelectrical signals (for example, myoelectric potential signals, neurotransmission signals, and brain wave signals) which are generated when the wearer wearing the motion-assist device 10 moves muscles around his/her joints. For example, in the present embodiment, a myoelectric potential sensor is used. Furthermore, in the present embodiment, the myoelectric potential sensor is attached so as to adhere to the skin surface around a joint of the wearer with an adhesive sticker covering the periphery of the electrode. In the present embodiment, signals detected by the myoelectric potential sensor adhering to the skin surface around a joint of the wearer (around a muscle used for moving the joint), are referred to as myoelectric potential signals. A body temperature measuring unit, for example, a temperature sensor for measuring the body temperature of thighs and shins, etc., produced by the motion of the doctor. An example is a thermistor that outputs body temperature detection signals indicating the body temperature. An angle detecting sensor can be a physical phenomenon detecting unit for detecting the rotational angle of the knee joint of the wearer (one of the physical phenomena). For example, an angle sensor such as a rotary encoder for counting the number of pulses proportional to the joint angle of the rods, and outputting, as the sensor output, electric signals in accordance with the number of pulses corresponding to the joint angle. Specifically, the angle sensor detects the rotational angle between two rods connected to the actuator unit/motor of device 10.

The controller runs code for calculating an output torque value based on the joint angle and output torque of the motion-assist device 10 (of the doctor), the joint angle and output torque of the motion-assist device 10 sent from the motion-assist device 10 of the patient, and the bioelectrical signals and the relative force of the motion-assist device 10. The calculated output torque value indicates the value of the torque to be output from the actuator unit or motor. Then, a signal corresponding to the calculated output torque value is supplied to a motor driver. Furthermore, the calculated output torque value is sent to the motion-assist device 10, together with the joint angle of the motion-assist device 10 that has been measured. The driver supplies power to the actuator unit or motor, so that the actuator or motor outputs torque corresponding to the output torque value output from the controller.

The communications module connected to the controller is a communications unit including communications equipment such as a communication modem and a router connected to a public line or the Internet, for sending various data items obtained by the motion-assist device 10 to the motion-assist device 10.

An application (app) is provided that receives information such as joint angles, muscle torque, motor torque, bioelectrical signals (for example, myoelectric potential signals, neurotransmission signals, cardiac potential signals, and brain wave signals), and body temperature; converts the information into graphs, diagrams, and values; and displays the conversion results. The information is not limited to being converted into a visual format such as a graph; the information may be converted into sound which is sent to the doctor. Furthermore, the information display device 31 may be combined with the motion-assist device as a single unit.

Each of these driving motors is an electric motor such as a DC motor or an AC motor whose driving torque is controlled by control signals from the control device. Furthermore, each of the driving motors includes a decelerating mechanism (built inside the driving unit) for decelerating the motor rotational speed by a predetermined reduction ratio, and can therefore generate a sufficient driving force despite the compact size. As a matter of course, the driving motor may be an ultrasonic motor having a thin shape so that it occupies a small space.

A belt-type waist fastening member can be worn around the hips of the wearer with batteries as power sources for driving the driving motors. The batteries are rechargeable type batteries, and are provided separately on the left and right so as not to hamper the walking motion of the wearer.

These biological signal detecting sensors are biological signal detecting units for detecting bioelectrical signals such as myoelectric potential signals and neurotransmission signals through the skin, and each includes an electrode (not shown) for detecting a faint potential. In the present embodiment, the biological signal detecting sensors are attached so as to adhere to the skin surface of the wearer with adhesive stickers covering the peripheries of the electrodes.

The device can be used for following purposes:
It can be tied around a person's torso and legs and help the person get up from the bed or toilet, or seat.
It can be used in lower scale and tied around a person's knee or Elbow to help it move.
The motivation for this idea has been that my grandparent cannot get up from the toilet seat and there is no help in the market except chairs with handles.

Figure 2:
FIG. 2 shows an exemplary motion assist system supporting a user.

FIG. 2 shows an exemplary motion assist system supporting a user. The black lines represent two metal-rods attached to the user. Ideally these rods are controlled by a motor which allows the rods to open and close to a desired angle essentially allowing the user to go from sitting down to standing up this motor is to be controlled by a smartwatch or smartphone and is intended to be used by those who have arthritis or have trouble bending over.

Figure 3:
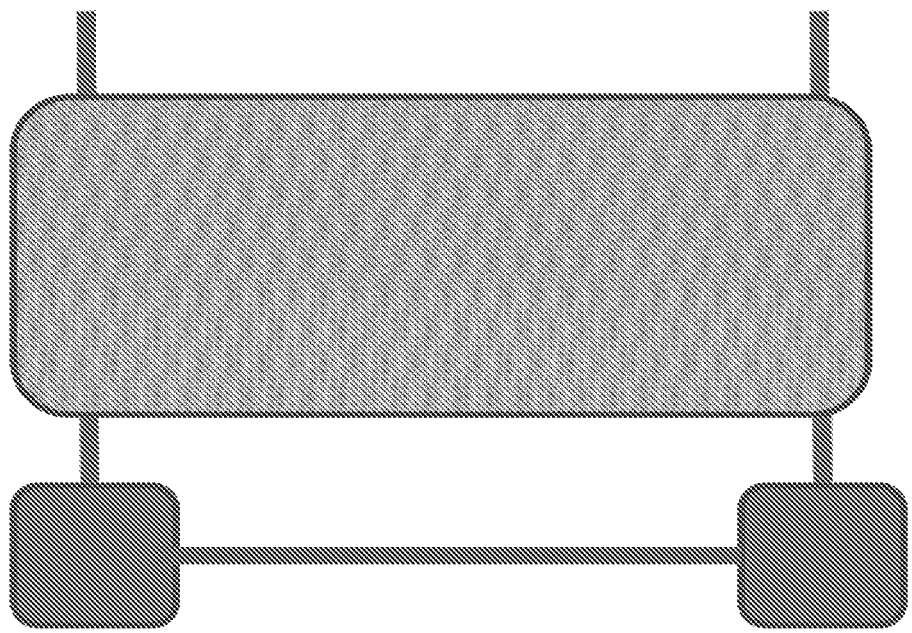
FIG. 3 shows a storage configuration of the device of FIG. 1. The device can be folded when it is not used. This configuration is compact to store and easy to carry when the user travels.

FIG. 3 shows a storage configuration of the device of FIG. 1. The device can be folded when it is not used. This configuration is compact to store and easy to carry when the user travels.

In one implementation, the rods can be attached to the outer side of the user's first leg, from the upper leg to the lower leg. In another embodiment, the leg attachment can be configured with a multi-rod mechanism having an upper rod, a lower rod and a foot rod (not shown). The upper end of the upper rod is coupled swingably to a hip rod via a first joint. The upper end of the lower rod is coupled swingably to the lower end of the upper rod, by using the second joint. The foot rod is coupled swingably to the lower end of the lower rod by a third joint. The upper rod is fixed to the user's upper leg, by a belt. The lower rod is fixed to the user's lower leg, by a belt. The foot rod is fixed to the user's foot, by a belt. The belt which fixes the foot rod is not depicted in the drawings. The hip rod is fixed to the user's trunk (hips).

Sensors can be disposed substantially coaxially to detect a pitch axis of the user's right hip joint, a pitch axis of the user's knee, and a pitch axis of the user's ankle. Each rod of the leg attachment can swing in accordance with the movement of the user's first leg. In each of the joints, the angle between the two adjacent rods which are coupled to that joint, and which include an encoder that detects the angle between the two rods, corresponds to the angle of the user's joint. In other words, the encoders detect the angles of the joints of the user. The encoder of the first joint detects the angle of the user's right hip joint around the pitch axis thereof. The encoder of the second joint detects the angle of the user's right knee joint around the pitch axis thereof. The encoder of the third joint detects the angle of the user's ankle joint around the pitch axis thereof. Below, the group of encoders installed at the respective joints may be referred to generally as angle sensors. A motion sensor can be attached to the rod 12. The motion sensor is installed in two locations at the front and rear of the leg. Another sensor such as a reaction force sensor or a load cell, which detects the load applied to the sole of the foot. This load corresponds to the floor reaction force received by the foot from the floor. The motor (actuator) 16 is installed on the second joint. The motor 16 can be disposed to the outside of the user's knee joint. The motor can be disposed coaxially with the user's knee joint. The motor can swing the lower rod relatively with respect to the upper rod. In one implementation, the motor 16 is able to apply torque to the user's right knee joint.

In one embodiment for remote maintenance of muscles, a doctor can remotely control the rods to cause predetermined leg or arm motions to be done so that the patient can learn to do the same motion as exercises. Alternatively, if the patient can't do the motion herself, the doctor can remotely move the leg/arm/body part as needed on a periodic basis to keep the patient body in proper form to avoid bed ridden muscle deterioration issues, for example. Information on physical phenomena at the motors/actuator units (for example, joint angles and output torque) is communicated between the motion-assist device 10 of the doctor and the motion-assist device 10 of the patient via the network. Various usage scenarios can include:

First embodiment (patient→doctor, patient←doctor, bidirectional communication): The rehabilitation is conducted with the doctor remotely controlling the motion-assist device 10 using a computer or a mobile device with an app, and the patient wearing the motion-assist device 10 (hereinafter, "first embodiment").

Second embodiment (patient→doctor): The doctor examines the patient as data (joint angles, torque, monitoring information, etc.) is sent from the motion-assist device 10 worn by the patient to the motion-assist device 10 of the doctor, so that the data is applied to or displayed on the motion-assist device 10 (hereinafter, "second embodiment").

Third embodiment (patient←doctor): The doctor conducts rehabilitation for the patient by moving a motion-assist device 10' worn by the doctor, so that data (joint angles, torque), which is sent from the motion-assist device 10, is supplied to and applied to the motion-assist device 10 (hereinafter, "third embodiment").

In one embodiment, the motion-assist device 10 of the patient receives the detection signals (detection data) of physical phenomena such as joint angles and output torque values of the motion-assist device 10, which are sent from the motion-assist device 10 according to rehabilitation motions of the doctor. The received joint angles and output torque values of the motion-assist device 10 are applied to the motion-assist device 10 itself (of the patient), based on the joint angles and output torque values of the motion-assist device 10 itself.

When the motion-assist device 10 of the patient moves, the motion-assist device 10 of the doctor receives the detection signals (detection data) of physical phenomena such as joint angles and output torque values of the motion-assist device 10 which are sent from the motion-assist device 10. Then, the received joint angles and output torque values of the motion-assist device 10 are applied to the motion-assist device 10 itself (of the doctor), based on the joint angles and output torque values of the motion-assist device 10 itself.

When the doctor remotely moves the motion-assist device 10 to conduct rehabilitation, the motion is immediately applied to the motion-assist device 10 worn by the patient, so that the rehabilitation is implemented. The doctor can physically perceive the state of the motion-assist device 10. Accordingly, the doctor can precisely recognize, in a real-time manner, the state of the patient with the motion-assist device 10. The doctor further moves the motion-assist device 10 with reference to the state of the patient in a real-time manner thus recognized, so that the rehabilitation is conducted more effectively.

According to one embodiment, a control unit of another one of the motion-assist devices controls a driving unit based on data transferred by a data transfer unit, such that a motion of the other one of the motion-assist devices corresponds to a motion of one of the motion-assist devices. For example, a doctor or a physical therapist can use the motion-assist device to objectively recognize the state of the target of motion assistance such as a patient or a trainee. Accordingly, motion assistance such as rehabilitation and training can be effectively performed, and the target of motion assistance such as a patient or a trainee can directly receive instructions of motion assistance from a doctor or a physical therapist. Furthermore, even when the doctor and the patient are at remote locations from one another, instructions for motion assistance can be transmitted and received via a communications unit, and the doctor can sense the motion of the target of motion assistance in response to the instructions.

In one embodiment, the system may provide a motion-assist system of a motion-assist device, the motion-assist device including a biological signal detecting unit configured to detect a biological signal generated in accordance with a motion of a wearer of a motion-assist tool included in the motion-assist device; a physical phenomenon detecting unit configured to detect a detection signal corresponding to a physical phenomenon in accordance with the motion of the wearer; a driving unit configured to apply assistance power to the motion-assist tool worn by the wearer; and a control unit configured to control the driving unit to generate the assistance power, by performing a calculation process based on the detection signal detected by the physical phenomenon detecting unit, the motion-assist system including a communications unit configured to connect together a plurality of the control units of a plurality of the motion-assist devices such that communications can be performed therebetween; and a data transfer unit configured to transfer data corresponding to at least one of the signals acquired in one of the motion-assist devices, to another one of the motion-assist devices via the communications unit, wherein the control unit of the other one of the motion-assist devices controls the driving unit based on the data transferred by the data transfer unit, such that a motion of the other one of the motion-assist devices corresponds to a motion of the one of the motion-assist devices.

Another embodiment may provide a motion-assist device worn by a wearer for performing communications with another motion-assist device worn by another wearer, to instruct the other motion-assist device to perform motion assistance or to perform motion assistance based on instructions from the other motion-assist device, the motion-assist device including an angle control output torque calculating unit configured to receive a joint angle of the other wearer of the other motion-assist device sent from the other motion-assist device, and to calculate an angle control output torque for the other motion-assist device, based on the received joint angle of the other wearer and a joint angle corresponding to the received joint angle of the other wearer of the other motion-assist device; a force control output torque calculating unit configured to receive an output torque of the other motion-assist device sent from the other motion-assist device, and to calculate a force control output torque for the other motion-assist device based on the received output torque; an assist control output torque calculating unit configured to calculate an assist control output torque based on an output torque of an actuator unit of the motion-assist device, the joint angle of the motion-assist device, a bioelectrical signal corresponding to a muscle force generated by the wearer, and a relative force applied to a frame of the motion-assist device; an output torque calculating unit configured to calculate an output torque for the other motion-assist device of the other wearer, based on at least one of the calculated angle control output torque and the calculated force control output torque, and the calculated assist control output torque; and a control unit configured to control the actuator unit of the motion-assist device in accordance with the calculated output torque.

Yet another embodiment may provide a motion-assist method of a motion-assist device, for performing communications with another motion-assist device worn by another wearer, to instruct the other motion-assist device to perform motion assistance or to perform motion assistance based on instructions from the other motion-assist device, the motion-assist device including the steps of receiving a joint angle of the other wearer of the other motion-assist device sent from the other motion-assist device, and calculating an angle control output torque for the other motion-assist device, based on the received joint angle of the other wearer and a joint angle corresponding to the received joint angle of the other wearer of the other motion-assist device; receiving an output torque of the other motion-assist device sent from the other motion-assist device, and calculating a force control output torque for the other motion-assist device based on the received output torque; calculating an assist control output torque based on an output torque of an actuator unit of the motion-assist device, the joint angle of the motion-assist device, a bioelectrical signal corresponding to a muscle force generated by the wearer, and a relative force applied to a frame of the motion-assist device; calculating an output torque for the other motion-assist device, based on at least one of the calculated angle control output torque and the calculated force control output torque, and the calculated assist control output torque; and controlling the actuator unit of the motion-assist device in accordance with the calculated output torque.

In another embodiment, the controller can assist the patient in walking. The controller of motor 16 stores a target trajectory for transferring from walking to a halt state, in addition to the target trajectory for the walking motion. The target trajectory for transferring from walking to the halt state will not be described herein. The controller acquires sensor data from the angle sensors and the reaction force sensor. The controller then estimates the relative position of the one foot with respect to the hip, in the horizontal front/rear direction, from the sensor data of the angle sensors. The relative position is determined from the hip joint angle and the knee joint angle around the pitch axes. Next, the controller judges whether or not the first leg is a standing leg. This judgment is based on deciding whether or not the detected floor reaction force is greater than a predetermined threshold value and then the leg is judged to be the standing leg, and if this is not the case, then the leg is judged to be an idling leg.

The present system is not limited to the specifically disclosed embodiment, and variations may be made without departing from the scope of the present system. Furthermore, various systems may be achieved by appropriately combining plural elements disclosed in the above embodiments. For example, some of the elements may be eliminated from each embodiment. Furthermore, elements of different embodiments may be appropriately combined.

What is claimed is:

1. A method for assisting body motion, comprising:
attaching a plurality of rods to a body with at least five rods are placed in an H-configuration and actuated by two motors, one motor on each leg of the H configuration, wherein each leg comprises two rods moved by the motor;
sensing movement parameters with sensors coupled to the rods;
transmitting the movement parameters to a wearable device and receiving actuation commands from the wearable device; and
based on the received commands, actuating the rods with one or more actuators.

2. A system for assisting body motion, comprising:
a plurality of rods with at least five rods are placed in an H-configuration and actuated by two motors, one motor on each leg of the H configuration, wherein each leg comprises two rods moved by the motor;
sensors coupled to the rods to sense movement parameters;
a wireless module to transmit the movement parameters to a wearable device and receive actuation commands from the wearable device; and
one or more actuators to move the rods according to the received actuation commands.

3. The system of claim 2, comprising a wearable device or a smart watch to communicate with the actuators.

4. The system of claim 2, comprising a wearable device that controls power, rate of opening or closing and direction of the rods.

5. The system of claim 2, wherein the wireless module receives actuating commands over a wireless network or a wired network.

6. The system of claim 2, wherein the wireless module receives actuating commands from a rehabilitation specialist operating remotely from the wearable device.

7. The system of claim 2, comprising a cloth mesh coupled to a pair of rods for providing a grip between the device and the patient.

8. The system of claim 2, wherein the rods support a buttock and a back.

9. The system of claim 2, wherein the rods are configured to attach to a person's knee or elbow to help mobility of the knee or elbow.

10. The system of claim 2, wherein the rods are folded to minimize storage space when not on a person.

11. The system of claim 2, wherein the sensors are disposed substantially coaxially to detect a pitch axis of a right hip joint, a pitch axis of a knee, and a pitch axis of an ankle.

12. The system of claim 2, wherein the sensors comprise strain gauge sensor, temperature sensor, thermistor, and bioelectric potential sensor.

13. The system of claim 2, comprising a rod connecting the two legs, wherein the rod is width-adjustable.

14. The system of claim 2, wherein the motors move in lock-step.

15. A system for assisting body motion, comprising:
a plurality of rods with at least five rods are placed in an H-configuration and actuated by two motors, one motor on each leg of the H configuration, wherein each leg comprises two rods moved by the motor;
a force sensor is disposed at a hinge that bends from a driving torque from the actuator unit;
a wireless module to transmit the movement parameters to a wearable device and receive actuation commands from the wearable device;
one or more motors actuated in lock-step to move the rods according to the received actuation commands; and a rod connecting the two legs, wherein the rod is width-adjustable.

\* \* \* \* \*